United States Patent [19]

Muehllehner et al.

[11] 4,057,727
[45] Nov. 8, 1977

[54] POSITRON IMAGING SYSTEM WITH IMPROVED COUNT RATE AND TOMOGRAPHIC CAPABILITY

[75] Inventors: Gerd Muehllehner, Mount Prospect; Michael P. Buchin, Schaumburg, both of Ill.

[73] Assignee: G. D. Searle & Co., Skokie, Ill.

[21] Appl. No.: 734,797

[22] Filed: Oct. 22, 1976

[51] Int. Cl.² .................. G01T 1/164; G01T 1/20
[52] U.S. Cl. ........................... 250/363 S; 250/366; 250/369
[58] Field of Search .............. 250/363 S, 366, 369

[56] References Cited

U.S. PATENT DOCUMENTS

| | | | |
|---|---|---|---|
| 3,329,814 | 7/1967 | Anger | 250/363 S X |
| 3,573,458 | 4/1971 | Anger | 250/369 X |
| 3,955,088 | 5/1976 | Muehllehner et al. | 250/363 S |

Primary Examiner—Archie R. Borchelt
Attorney, Agent, or Firm—Walter C. Ramm; Albert Tockman; Dennis O. Kraft

[57] ABSTRACT

A positron imaging system and method in which two opposed Anger cameras are employed on opposite sides of an organ to be imaged. The cameras include a planar unitary scintillation crystal approximately one inch in thickness, and the electronics which process the signals from the cameras include pulse shaping circuitry to reduce both the duration and the integration time of pulses resulting from radioactive events. Both cameras exclude collimators to enable radiation incident upon them at many angles to be accepted, and means are included to rotate the opposed cameras about the organ of interest to enable transverse tomographic imaging.

11 Claims, 5 Drawing Figures

COUNT RATES USING DISTRIBUTED SOURCE IN AIR

|  | 1/2 in. Crystal × $10^3$ cts/sec. | 1 in. Crystal × $10^3$ cts/sec. |
|---|---|---|
| $N_s$ | 124 | 155 |
| $N_c$ | 6.8 | 12.4 |
| $N_{pp}$ | 0.75 | 2.67 |
| $N_{pc,cp}$ | 1.89 | 3.44 |
| $N_{cc}$ | 1.45 | 1.2 |

$N_{pp}$ = PHOTOPEAK-PHOTOPEAK COINCIDENT EVENTS
$N_{pc,cp}$ = PHOTOPEAK-COMPTON, COMPTON PHOTOPEAK COINCIDENT EVENTS
$N_{cc}$ = COMPTON-COMPTON COINCIDENT EVENTS
$N_s$ = SINGLES EVENTS
$N_c$ = COINCIDENT EVENTS

POSITRON IMAGING SYSTEM WITH IMPROVED COUNT RATE AND TOMOGRAPHIC CAPABILITY

BACKGROUND OF THE INVENTION

The present invention relates to imaging devices for detecting a radiation distribution due to positron annihilations in an organ of interest of a living subject.

Although positron imaging enables the use of a whole new class of radiopharmaceuticals of great physiological significance, the development of the appropriate instrumentation has lagged compared, for example, to gamma imaging. Positron imaging devices can be grouped into two categories: (a) those using a multiplicity of discrete detector units, and a similar multiplicity of coincident circuits to accommodate these detectors; and (b) those using at least one Anger-type scintillation camera having a single crystal, together with a second detector, and a single coincidence circuit. An early report by H. O. Anger printed for the U.S. Atomic Energy Commission entitled "Scintillation in Positron Cameras" (UCRL-8640, Aug. 12, 1959) applies the underlying concept of the original Anger scintillation camera (see U.S. Pat. No. 3,011,057) with some appropriate modifications and alterations to detect positron events.

Regardless of the category of system, the goals are identical; that is, to achieve high sensitivity and resolution, and at the same time high count rate capability. Although the camera-based systems are generally superior in resolution, heretofore they have lacked count rate capability comparable to the discrete detector systems (see for example H. O. Anger, "Radioisotope Cameras: Instrumentation in Nuclear Medicine", Vol. 1, G. J. Hine, Editor, New York, Academic Press, 1967; G. L. Brownell and C. A. Burham, "Recent Developments in Positron Scintigraphy: Instrumentation in Nuclear Medicine", Vol. 2, G. J. Hine and J. A. Sorenson, Editors, New York, Academic Press, 1973; and P. J. Kenny, "Spatial Resolution and Count Rate Capacity of a Positron Camera: Some Experimental and Theoretical Considerations", International Journal of Applied Radiation and Isotopes, Vol. 22, Permagon Press, Pages 21-28, 1971). The results of the above investigations have lead to the conclusion that the useful count rate capability of a positron camera is only a small fraction of the actual count rate.

Accordingly, the interest by other workers has been biased toward development of discrete detector positron devices. Recently, the first commercial availability of positron devices has been of the discrete detector type: a device developed by Dr. G. Brownell is offered by Cyclotron Corporation, and a system developed by Drs. M. Phelps and M. Ter Pogossian is offered by Ortec, Inc. Although both devices have good count rate capability, they are limited in sensitivity, resulting in long imaging times with many tagged pharmaceuticals of interest.

Meanwhile, efforts have continued at development of an improved Anger camera-based positron imager. One recent development of importance has been the invention of graded radiation absorbers with plural coincidence channels for the Anger detectors, to enable both the primary radiation as well as the Compton events, which formerly would have been lost, to be processed, thereby improving the overall count rate. See U.S. Pat. No. 3,955,088, the disclosure of which is incorporated herein by reference.

The advent of tomographic imaging in other imaging modalities, especially X-ray, has made the achievement of satisfactory count rates of still greater importance. Indeed, transverse tomographic imaging has not heretofore been fully successful for Anger camera positron devices because of the sensitivity and count rate problem and because of the need for better data processing. It has been attempted, for example, to implement a rotational transverse mode by adding collimators consisting of parallel slits to a pair of opposed camera detectors, rotating, then utilizing the same algorithms and reconstruction techniques as in X-ray computerized tomography. But it has been found that the collimators reduce sensitivity and counting statistics too drastically for such a system to be of any great general utility.

The above-mentioned discrete detector-based imagers have also been used in attempts to provide a rotational transverse mode, but the devices so far produced have been of limited capability due to the need for irises or other collimation, the possibility of only a limited number of resolution points over the detector arrays, the lack of continuity between image slices, and the capability for only one or at best a few image slices simultaneously per scan.

SUMMARY OF THE INVENTION

Accordingly, it is an object of the invention to improve the sensitivity and count rate capability of Anger camera-based positron imaging systems.

It is also an object of the invention to improve the scintillation crystal and pulse processing electronics of the positron camera to improve count rate capabilities.

It is another object of the invention to avoid the limitations of collimators upon count rate capability and sensitivity in positron imaging system.

It is a further object of the invention to provide an Anger camera positron imaging system which avoids the use of collimators.

It is yet another object of the invention to provide a positron imaging Anger camera device capable of satisfactory transverse tomographic imaging.

In a broad aspect the invention is, in a positron imaging system with improved count rate capabilities for detecting the radioactive distribution of positron events within an organ of interest of a living subject, and which includes scintillation detectors producing electrical signals in response to the positron events as well as electronic means for processing the electrical signals and for supplying image reconstruction signals to a display means to produce an image of the radioactive distribution, the improvement which comprises a pair of Anger-type scintillation cameras as the scintillation detectors, each camera being respectively positioned on opposite sides of the organ of interest; and pulse shaping means for reducing the pulse duration below approximately 900 nanoseconds, and for reducing the integration time below approximately 500 nanoseconds, whereby the count rate capability and the counting statistics of the system is improved for greater image quality and processing speed. In another aspect, the invention also includes means for rotating the opposed camera heads about an axis which passes through the organ of interest, and the cameras each exclude a collimator, enabling the acceptance of radiation not traveling within planes perpendicular to the planar scintillation crystals.

BRIEF DESCRIPTION OF THE FIGURES

The present invention may be described with greater clarity by reference to the accompanying drawings, in which.

DETAILED DESCRIPTION OF THE INVENTION

Figures 1, 3:
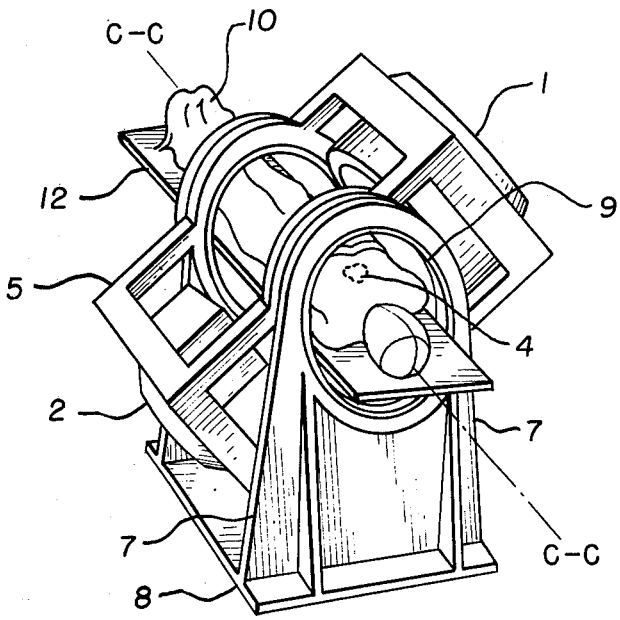
FIG. 1 is a perspective view of the mechanical portion of the system showing the rotatable support for the opposed cameras.
FIG. 3 is a table illustrating the improvements in count rate achieved with the present invention.

Referring now more particularly to the several figures, the device of FIG. 1 may be of the type utilizing two Anger scintillation camera heads 1 and 2 positioned on opposite sides of an organ 4 of a living subject which is desired to be imaged, and at roughly equal distances from organ 4. The basics of such a symmetrically-arranged imaging system may be found in the above-mentioned Kenny paper. As may be seen in FIG. 1, the appropriate roughly equal distances and opposed orientation of the two cameras are maintained by a rigid open box frame 5, with the camera heads 1 and 2 being secured at opposite ends of such box frame. The frame 5 is journaled midway of heads 1 and 2 within the upright legs 7 of a rigid U-shaped floor stand 8. As is apparent, the frame 5 is journaled upon stand 8 with large hollow cylindrical bearings 9 of open inside diameter sufficient to allow passage therethrough of a patient 10 lying supine upon a suitable table 12. Although the table is shown only schematically, the construction of such patient support tables is quite well-known in the art. In this manner, an organ located anywhere within the body of the patient may be imaged.

The foregoing arrangement enables the opposed camera heads 1 and 2 to be rotated in a generally circular orbit about a horizontal axis C—C, which generally coincides with the cranial-caudal axis of the patient. Driving the head framework 5 in stand 8 is a motor 14 (see FIG. 2) mounted on stand 8. Motor 14 cooperates with a shaft position encoder 16, which detects the angle and degree of completion of a rotation of the heads 1 and 2 and provides a signal representative of this information. Motor 14 also includes an indexing means 17 for continuously advancing the heads 1 and 2 through their orbit. The indexing means initiates and terminates radiation counting intervals at any predetermined arc interval in the orbit.

Each of the heads 1 and 2 is conventional in that it includes the respective disc of scintillator crystal of thallum activated sodium iodide approximately 15 inches in diameter, respective arrays of photodetectors arranged to view overlapping areas of associated scintillators, and scintillation position-identifying circuitry. However, the camera heads are also unconventional in other respects. The camera heads are equipped with scintillation crystals which are appreciably thicker than those employed previously for positron imaging, as well as those normally employed for routine gamma imaging work. It will be appreciated from prior art that typical crystal thicknesses range downwardly from approximately ½ inch.

Uniformity and resolution are normally considered to be adversely affected by increased crystal thickness. However, it has been found that in the context of two opposed Anger cameras in a positron imaging mode, uniformity and resolution are not unacceptably affected by the thick crystal. There is, for example, no one-to-one correspondence between a particular point in either crystal, and a point in the image. Yet the added thickness provides a distinct improvement in count rates and sensitivity. This is because the additional thickness serves to increase the probability of a scintillation-producing interaction with the crystal at the predominant energies of interest. For example, the probability of one or more Compton interactions followed by a photoelectric interaction is more then doubled with the increased thickness.

Figure 2:
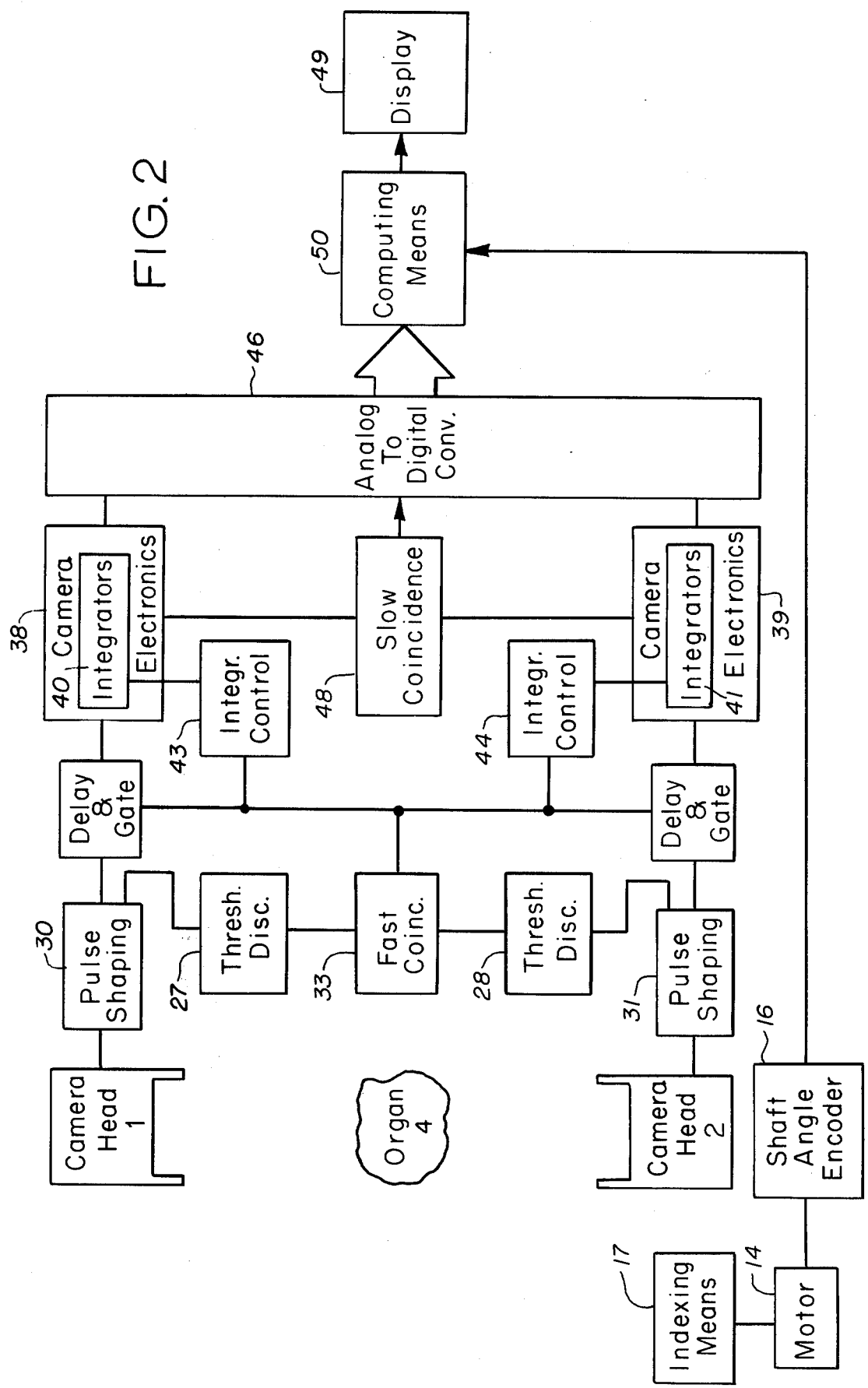
FIG. 2 is a block diagram of the entire positron imaging system.

Each of the photodetector arrays is connected to a respective one of the threshold discriminator circuits 27 and 28, via respective pulse shaping circuits 30 and 31, as may be seen with more particularity in FIG. 2. If the combined magnitude of the electrical pulses from each photodetector array exceeds a threshold magnitude established by the discriminators 27 and 28, an output is provided through the fast coincidence detection circuit 33. Upon detecting a coincidence scintillation in the two cameras, coincidence circuit 33 provides an enabling output to each of two delay and gate circuits 35 and 36, each of which is also connected to the ouput of a respective one of the photodetector arrays.

Delay and gate circuits 35 and 36 prevent output pulses from the camera detectors from being further processed by the system unless an enabling signal is recieved from coincidence detector 33, thus verifying that the signal results from a positron annihilation event. Since the coincidence analysis requires a finite amount of time, delay and gate circuits 35 and 36 also impose a predetermined degree of delay on incoming signal pulses to insure matching the enabling signal from coincident detector 33 with the proper incoming pulses.

The signals from each delay and gate 35 and 36 are then gated into a respective camera electronics circuit 38 and 39, which are generally conventional circuit calculating the position in rectilinear coordinates of an interaction in the crystals 18 and 20 which gave rise to a scintillation in the crystals. The camera electronics include integrators 40 and 41 for each signal component received from photodetector arrays 22 and 23. Integrators 40 and 41, which may, for example, be operational amplifiers, are controlled by means of integration controls 43 and 44 respectively, to enable cutting the time of integration for the individual signal pulses. In the case of an op-amp integrator, for example, the control adjusts a pulse width which gates the input to the op-amp integrator.

At this point it should be noted that the pulse shaping circuits 30 and 31 and integrators 40 and 41 with associated controls 43 and 44 provide a means of redressing the limitations on count rate capability of the instrument imposed by the inherent time constant of the crystal, and subsequent inherent pulse duration of the individual events being processed. Pulse shaping circuits 30 and 31, which are preferably pole zero cancellation filters, but which can be of other design as well, shorten the duration of pulses, eliminating long pulse decay "tails". Thus prior events do not persist to interfere with or block the detection of subsequently arriving events. At elevated rates of data arrival, it will be appreciated that many more events per unit time will be detected as a result. Standard camera configurations operate with an approximately 900 nanosecond pulse duration; in the present device, a 500 nanosecond clipped pulse is used as a result of pulse shaping circuits 30 and 31 with improved results.

Similarly, another point in the system in which the persistence of a prior event, and its processing causes the loss of a subsequent event is at the above-mentioned integrators 40 and 41. With the controls 43 and 44 adjusted to reduce the integration interval, so that the integration time for the individual pulse representing a prior event is reduced, more of the subsequently arriving pulses will be processed, rather than being lost in "pile up" effects. It will be appreciated that the improvement will be of greater importance at elevated rates of data arrival. In standard cameras, a 900 nanosecond integration interval is typical, while in the present device, a 350 nanosecond interval is employed. The count rate performance because of such pulse shaping and pulse integration shortening has been found to be improved by at least a factor of two. Further details regarding the techniques may be found in G. Amsel et al., "Shortening of Detector Signals with Passive Filters for Pile-up Reduction", Nuclear Instruments and Methods, 71 (1969) 1–12, North Holland Publishing Company; and C. Brassard, "Fast Counting with NAI Spectrometers", Nuclear Instruments and Methods, 94 (1971) 301–306, which are incorporated herein by reference.

Such techniques have heretofore been confined only to certain highly specialized applications, and have not been applied to standard Anger camera imaging because the techniques normally cause a very objectionable degradation of resolution with poorer statistics. However, in applications to the dual Anger camera positron context, these techniques have been discovered not to cause such objectionable degradation, while vastly improving count rate performance.

Each of camera electonics circuits 38 and 39 provide an output to analog-to-digital convertor 46, as well as to slow coincidence means 48. The latter is a generalized term for the electronics improvements as detailed in the aforementioned U.S. Pat. No. 3,955,088. Briefly summarized, slow coincidence means 48 includes a plurality of single channel analyzers for each of the outputs, defining a plurality of discrete channels or windows of acceptable energy ranges. One of the windows is centered about 511 KEV, the photopeak, and another spans a broader energy range wherein Compton events predominate. A gating circuit receiving the inputs from the single channel analyzers pertaining to both cameras provides a trigger output when sensing coincidences between a signal in any of the channels associated with camera 1 with a signal in any of the channels associated with camera 2, thus allowing all combinations of photopeak events and Compton event coincidences to result in an output trigger. The analog-to-digital convertor 46 processes the signals from camera electronics 38 and 39 only if such signals also cause slow concidence means 48 to produce a trigger signal to the analog-to-digital convertor. The ADC when thus gated converts the heretofore analog signals to digital form, and passes them to calculating means 50 (to be further described below), which then inputs display 49 to image the object.

It is instructive to refer to FIG. 3, which summarizes the kind of improvement in count rate performance which can be expected with the present system. It should be noted that such improved performance is due not only to the just-mentioned electronics, but also to the thicker crystals, and to the graded absorbers with slow coincidence electronics which are the subject of above-referenced U.S. Pat. No. 3,955,088. From the table of FIG. 3, it may be seen that the previous systems with one-half inch crystals are compared in various performance categories with the present system in detection of positron sources of the same activity. It may be seen that as compared to using a prior system detecting photopeak-photopeak coincidences, the overall gain to be had from using the present system, detecting all combinations of photopeak and Compton events except Compton-Compton coincidences (excluded because of their lower resolution), is 6.11/.75, or a factor of 8. At the same time, the singles rate, a measure of non-coincident events falsely counted as coincident positron events, has increased by only 25 percent.

The above described improvements enhancing count rate are especially important in transverse tomographic imaging applications, wherein the opposed camera heads are rotated about an axis C—C generally coinciding with the cranial-caudal axis of the patient, as shown in FIG. 1. In such an imaging mode, the system images one or more parallel "slices" of the internal structure of the patient, lying in planes transverse to the cranial-caudal axis. Because of the much greater amount of information which is thereby sought to be imaged, the transverse tomographic mode requires higher count densities than with ordinary longitudinal views.

The previous practice of utilizing slit collimators, however, severely compromises sensitivity; and the count rate improvements, while helpful, do not address this basic problem. It has been found that the full advantages of the above count rate improvements become apparent in conjunction with still another improvement, which is to exclude collimators from the camera head when operating in the rotational transverse mode. A major source of image degradation, due to diminished sensitivity and count rate, is thus eliminated. Not only is radiation is accepted which travels in planes orthogonal to the scintillation crystals, but also radiation is accepted which travels at substantial angles to the crystals. With the added sensitivity and enhanced count rate provided by lack of collimators, and the aforementioned improvements, transverse tomographic positron imaging can now be satisfactory implemented.

Of course, since projections through the organ of interest are no longer restricted to lie in parallel planes as with parallel slit collimated systems, a large number of projections are obtained, particularly during rotation. A considerable problem exists of organization of the data developed by the cameras. The extent of the problem may be appreciated by the fact that each camera represents roughly 4,000 resolution elements. Each element may be in coincidence with each resolution element in the opposing detector; thus, $16 \times 10^6$ combination are possible even when both detectors are stationary. This number is increased on order of magnitude when all possible angles are included. Techniques for data organization used with devices having discrete detectors and limited coincidence channels are therefore not readily applicable. Indeed, due to the large number of coincidence channels which would be necessary to cover any substantial number of the possible coincidence combinations, it is unlikely that any such coincidence channel would have more than one count during a complete study. Much information would be lost if the resolution elements were made coarse enough to reduce the possible coincidence channels to a manageable number.

Accordingly, a more powerful data processing means is needed to enable full utilization of the capabilities of this system, if undue complexity and/or undue performance compromises are to be avoided. A suitable computing means 50, for example as made available by Interdata Corporation as Model-832, is therefore interfaced with ADC 46 and receives the digitalized outputs of camera electronics 38 and 39, as well as the output of shaft angle encoder 16, which senses and outputs a signal representative of the angular orientation of the detector head frame assembly 5. Not only must the location of each positron event in the organ of interest be determined, given the two camera coordinates of the coincidence scintillations which result from it, but also such information at a plurality of angular orientations must be assimilated and utilized for image reconstruction. The computing means allows these operations to be performed without loss of data and undue complexity.

Figure 4:
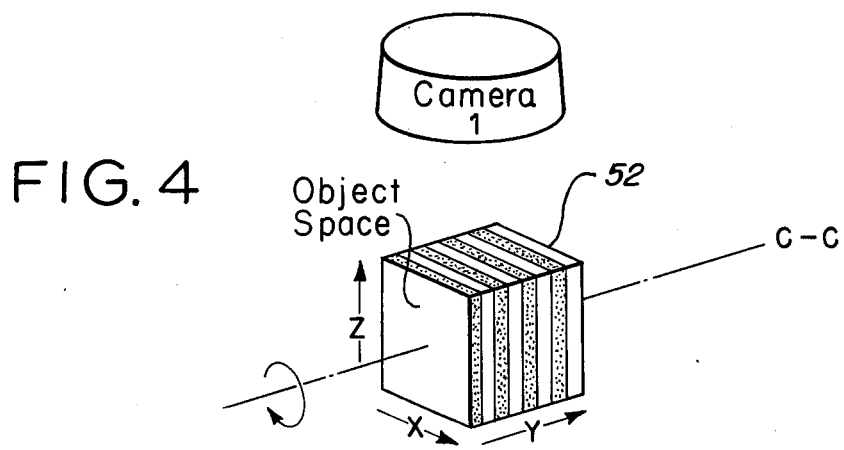
FIG. 4 illustrates the manner in which rotational transverse tomography is accomplished.

In accordance with well-known programming principles, the incoming data is processed by applying thereto on an event by event basis a method of back projection as detailed below, followed by applying a filtering or deconvolution to the back projection images. The geometry which is applied for such back projection and image reconstruction is as shown in FIG. 4. The object space 52 centered around cranial-caudial axis C—C has been partitioned into eight slices in the $y$-direction. Images are reconstructed in the $xz$ plane, i.e. transverse to the detector plane, but lying in the plane of rotation. The choice of eight slices is largely dictated by the size of memory available in the computing means 50. The device has high resolution in the $y$ direction, and the reconstruction technique is such that extending the number of slices does not increase computing time. At the same time, selecting a small number of slices assures adequate statistical information in each slice without excessive imaging time. The slices are furthermore chosen to lie in the plane of rotation so that each element in the image plane is imaged from all angles, thus assuring adequate angular sampling. Since, however, coincidences between the two camera heads 1 and 2 are not restricted in the $y$ direction, projections are obtained which transverse several slices, and the filter or convolution function used for imagery construction cannot, therefore, be restricted to a single slice, but rather extends to several slices.

Figure 5:
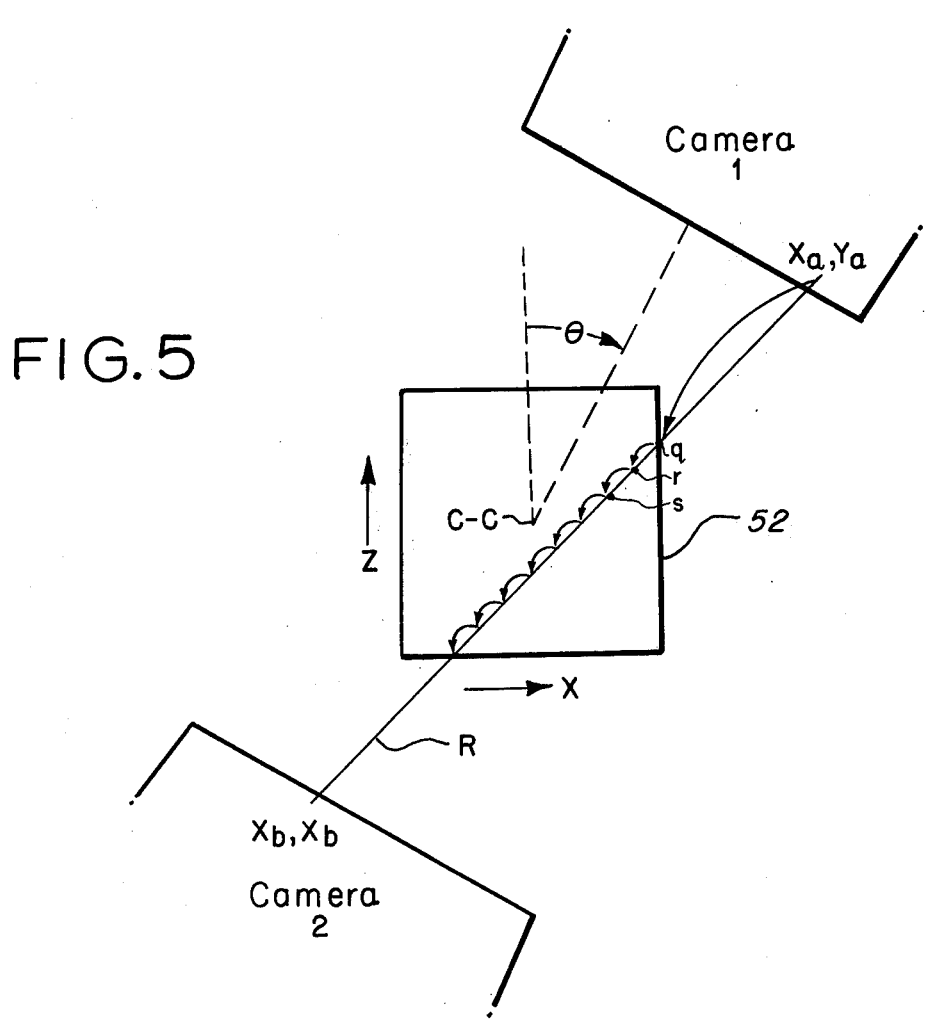
FIG. 5 is an illustration of the technique used for reconstruction of the image of the object.

The method of back projection is shown in FIG. 5; for simplicity a projection though a single slice, i.e. $y_a = y_b$ is shown. For any arbitrary angle of rotation $\theta$, a positron event is defined by coincident scintillations $a$ and $b$, representing, for example, the interaction of two oppositely travelling gamma rays resulting from the positron event. These scintillations $a$ and $b$ are located at camera coordinates $x_a'\ y_a'$ for camera head 1 and $x_b'\ y_b'$ for camera head 2. These are converted to object coordinates $x'\ y'\ z'$ though the transformation:

$$x_a' = (s/2) \sin \theta + x_a \cos \theta$$

$$y_a' = y_a$$

$$z_a' = (s/2) \cos \theta - x_a \sin \theta$$

$$x_b' = -(s/2) \sin \theta + x_b \cos \theta$$

$$y_b' = y_b$$

$$z_b' = -(s/2) \cos \theta - x_b \sin \theta$$

where $s$ is the separation between detectors.

The straight line connecting the two points $x_a$ and $y_a$ and $x_b\ y_b$, or after transformation $x_a'$, $y_a'$ and $x_b'$, $y_b'$, represents the back projected ray R. Because the back projected reconstruction of an ideal point source with both detectors stationary looks like two conical volumes arranged tip to tip, the geometry is termed "cone beam geometry".

Locations in the memory of computing means 50 are associated with corresponding locations in the actual object space 52, as well as with the predetermined number of "slices", in this case eight, as mentioned above. Points within the object space 52 are calculated at equal distances $q$, $r$, $s$, etc. along the ray R. The $xyz$ coordinates of each such point are truncated, after which the content of the corresponding memory location is incremented by "one". This technique assures equal projected density along the path and avoids time consuming calculations involving the volume of overlap between each element and a cylindrical volume surrounding the ray, as is sometimes done in two dimensional back projection.

It should be noted that on a given back projected ray, some memory locations may well be incremented twice, particularly if the ray traverses the object space 52 along a diagonal, a condition which results from the requirement of equal density along the ray. Not only may the back projection be executed in real time with an on-line computing means, but also processing may, of course, be performed off-line, using magnetic tape to record all camera coordinates of the detected positron events. A three dimensional filter or convolution is then applied to the back projected image, to obtain the object distribution of positron radioactivity. The display 49 may then image any of the predetermined number of slices, or a plurality simultaneously on different respective portions of the screen.

We claim:

1. In a positron imaging system with improved count rate capability for detecting the radioactive distribution of positron events within an organ of interest of a living subject, and including scintillation detectors producing electrical signals in response to said events, electronic means for processing said electrical signals and for supplying image reconstruction signals to a display means to produce an image of said radioactive distribution, the improvement comprising:

a pair of Anger-type scintillation cameras as said scintillation detectors, each camera having a unitary planar scintillation crystal, said crystal being greater than one-half inch in thickness, said cameras being respectively positioned on opposite sides of said organ; and pulse shaping means for reducing the pulse duration below approxmatley 900 nanoseconds, and for reducing the integration time of said pulse below approximately 500 nanoseconds, whereby the count rate capability and counting statistics of the system is improved for greater image quality and processing speed.

2. A positron imaging system as in claim 1, in which said crystal is approximately 1 inch thick.

3. A positron imaging system as in claim 1, in which said pulse shaping means include a plurality of wave shaping filters, each in series with an output of each of said cameras.

4. A positron imaging system as in claim 3, in which said pulse shaping means further includes adjustable integrator means receiving the portion of the camera outputs which have been verified as representative of positron events, and control means for said integrator means for adjusting the time of integration for said signals.

5. A positron imaging system as in claim 1, in which said improvement further comprises means for rotating said opposed heads about an axis which passes through the organ of interest.

6. A positron imaging system as in claim 1, in which said cameras each exclude a collimator, enabling acceptance of radiation not traveling within planes perpendicular to said planar scintillation crystals.

7. In a positron imaging scintillation system for detecting the radioactive distribution of positron events within an organ of interest of a living subject, and including scintillation detectors producing electrical signals in response to radiation, electronic display means, electronic means for processing said electrical signals and for supplying reconstruction signals to said display means to produce an image of said radiation distribution of positron events, the improvement which comprises a pair of Anger-type scintillation cameras as said scintillation detectors, each having a unitary planar scintillation crystal, said cameras being respectively positioned on opposite sides of said organ, both of said cameras excluding collimators to accept radiation not traveling within planes perpendicular to said scintillation crystals; coincidence circuitry means monitoring the output of both of said cameras and providing validation signals to said signal processing means to identify those pulses associated with positron events; and means for rotating said opposed heads about an axis which passes through said organ of interest.

8. A positron imaging scintillation as in claim 7, in which said planar scintillation crystal is greater then $\frac{1}{2}$ inch in thickness.

9. A positron imaging scintillation system as in claim 7, in which said signal processing means includes means for reducing the duration and integration time of said signal pulses.

10. A method of positron imaging for detecting the radioactive distribution of positron events within an organ of interest within an living subject, for use with a pair of opposed Anger-type scintillation cameras and electrical means for processing the signals from said camera and for supplying image reconstruction signals to a display means, said method comprising:
viewing the organ of interest with said two cameras with said organ positioned between said opposed detectors;
rotating said opposed scintillation cameras about the organ of interest;
evaluating the electrical pulses produced by said cameras by means of coincidence circuitry to identify signal pulses from one camera which are coincident with signal pulses from the other camera;
providing said signal processing means with a validation signal to idenitfy said coincident signal pulses, whereby said coincident signals are selectively processed by said processing means;
and reducing the duration and integration time of said signal pulse to improve the count rate capability and thereby the quality of the resultant image.

11. A method as in claim 10, which includes the further step of accepting from said organ of interest radiation traveling not only in planes orthogonal to said scintillation crystals, but also in planes not orthogonal to said crystal.

* * * * *